United States Patent
Al Rasheed et al.

(10) Patent No.: US 8,673,003 B1
(45) Date of Patent: Mar. 18, 2014

(54) METHOD FOR IMPROVING THE EARLY DETECTION OF BREAST CANCER AND DEVICE THEREFOR

(76) Inventors: Abdullah Khalid Al Rasheed, Ryadh (SA); Sami Abdulrahman Aldaham, Ryadh (SA)

( * ) Notice: Subject to any disclaimer, the term of this patent is extended or adjusted under 35 U.S.C. 154(b) by 350 days.

(21) Appl. No.: 13/066,328

(22) Filed: Apr. 12, 2011

Related U.S. Application Data

(60) Provisional application No. 61/399,951, filed on Jul. 20, 2010.

(51) Int. Cl.
*A61F 2/12* (2006.01)

(52) U.S. Cl.
USPC .......................................................... 623/8

(58) Field of Classification Search
USPC ......................................................... 623/7–8
See application file for complete search history.

(56) References Cited

U.S. PATENT DOCUMENTS

| | | | | |
|---|---|---|---|---|
| 4,134,218 | A * | 1/1979 | Adams et al. | 434/267 |
| 4,867,686 | A * | 9/1989 | Goldstein | 434/267 |
| 5,716,407 | A * | 2/1998 | Knapp et al. | 128/898 |
| 6,214,045 | B1 * | 4/2001 | Corbitt et al. | 623/8 |
| 6,412,491 | B1 * | 7/2002 | Rusin | 128/897 |
| 2002/0172214 | A1 * | 11/2002 | Grantham | 370/431 |
| 2003/0192557 | A1 * | 10/2003 | Krag et al. | 128/898 |
| 2005/0000525 | A1 * | 1/2005 | Klimberg et al. | 128/898 |
| 2006/0264399 | A1 * | 11/2006 | Lim et al. | 514/54 |
| 2008/0281388 | A1 * | 11/2008 | Corbitt et al. | 607/108 |
| 2009/0024225 | A1 * | 1/2009 | Stubbs | 623/23.72 |
| 2009/0105582 | A1 * | 4/2009 | Dougherty et al. | 600/420 |
| 2010/0158934 | A1 * | 6/2010 | Jakobovits et al. | 424/185.1 |
| 2010/0178244 | A1 * | 7/2010 | Arnsdorf et al. | 424/1.29 |
| 2010/0178245 | A1 * | 7/2010 | Arnsdorf et al. | 424/1.29 |
| 2011/0077736 | A1 * | 3/2011 | Rofougaran | 623/8 |
| 2013/0012755 | A1 * | 1/2013 | Slayton | 600/2 |
| 2013/0017148 | A1 * | 1/2013 | Larsen et al. | 424/1.11 |

* cited by examiner

*Primary Examiner* — Suzette J Gherbi
(74) *Attorney, Agent, or Firm* — Ted Masters

(57) ABSTRACT

A device for improving the early detection of a malignant breast cancer tumor in the breast of a human being includes a foreign body implant which is shaped and dimensioned to imitate a breast tumor. The foreign body implant is implanted in the breast of a human being and provides a tactile standard with which to compare a possible actual breast cancer tumor. During periodic breast self examination, the human being feels the foreign body implant to reinforce a tactile memory of what breast tumors feel like.

3 Claims, 2 Drawing Sheets

METHOD FOR IMPROVING THE EARLY DETECTION OF BREAST CANCER AND DEVICE THEREFOR

CROSS REFERENCE TO RELATED APPLICATION

This application claims the filing benefit under 35 U.S.C. §119(e) of U.S. Provisional Application No. 61/399,951, filed Jul. 20, 2010, which is hereby incorporated by reference.

TECHNICAL FIELD

The present invention pertains generally to breast cancer, and more particularly to a foreign body implant which is implanted in the breast of a healthy human being to improve the patient's ability to detect breast cancer through breast self-examination.

BACKGROUND OF THE INVENTION

Breast cancer (malignant breast neoplasm) is cancer which develops in the human breast. Aside from non-melanoma skin cancer, breast cancer is the most common form of cancer in women. The risk of getting breast cancer increases with age. Early diagnosis of breast cancer usually results a good prognosis after treatment as compared with late diagnosis.

Breast self-examination (BSE) is a method used to detect early breast cancer. In this method the woman periodically feels each of her breasts in an attempt to find the lumps, swelling, or distortions associated with breast cancer. However, oftentimes self-examination is ineffective. In reference to the "Randomized trial of breast self-examination in Shanghai" study[1], the study's conclusion was as follows—{Intensive instruction in breast self examination (BSE) did not reduce mortality from breast cancer. Programs to encourage BSE in the absence of mammography would be unlikely to reduce mortality from breast cancer. Women who choose to practice BSE should be informed that its efficacy is unproven and that it may increase their chances of having a benign breast biopsy}.

The low effectiveness and accuracy of BSE is caused by many factors:
- The woman is looking for something (the tumor) which she has never touched in her life.
- Layers of adipose tissue separate the lump from the tips of the palpating fingers.
- Even with breast simulation model* training, the tactile memory will fade with time. Unfortunately, the level of skill and motivation required for effective BSE decline with time. *A breast simulation model is a life size reproduction of a human breast which simulates the feel of a real human breast having a cancer tumor, and upon which a woman may practice tactile cancer detection skills.
- A breast simulation model cannot simulate a real human breast with 100% accuracy.
- Unfortunately mammography is only 85% accuracy in diagnosis. Clinical breast examination (CBE) rather than BSE identifies some cancers missed by mammography and provides an important screening tool among women for whom mammography is not recommended or women who do not receive high-quality screening mammography according to recommended guidelines.[2]

REFERENCES

1—*J Natl Cancer Inst.* 2002 Oct. 2; 94(19):1445-57.
2—CA Cancer J Clin 2004; 54:345-361
doi: 10.3322/canjclin.54.6.345
©2004 American Cancer Society
Performance and Reporting of Clinical Breast Examination: A Review of the Literature
Sharon McDonald, Debbie Saslow, PhD and Marianne H. Alciati, PhD

BRIEF SUMMARY OF THE INVENTION

The present invention is directed to a foreign body implant (FBI) for improving the early detection of breast cancer and its method of use. The foreign body implant is implanted in the soft tissue of a human female breast to improve the early detection of breast cancer by providing a tactile standard with which to compare a possible breast cancer tumor. The foreign body implant improves both proficiency and effectiveness of BSE in the early detection of breast cancer. The foreign body implant is shaped and dimensioned to accurately simulate the shape and consistency of breast cancer nodules or lumps. In another possible but less effective embodiment, the foreign body implant is implanted in the soft tissue of the anterior abdominal wall. One of the unique features of the foreign body implant is that it is typically implanted in the breast of a healthy human being (one without breast cancer). As such, the foreign body implant and related method serve to provide early detection of possible tumors in persons who are cancer free before the implant.

In accordance with an embodiment of the invention, a device for improving the early detection of breast cancer tumor in the breast of a human being includes a foreign body implant which is shaped and dimensioned to imitate a breast tumor. The foreign body implant has an asymmetrical shape, and is implantable in the breast of the human being. The foreign body implant provides a tactile standard with which to compare a possible breast cancer tumor.

In accordance with another embodiment, the foreign body implant has a maximum dimension of about seven millimeters.

In accordance with another embodiment, the foreign body implant has an irregular surface.

In accordance with another embodiment, the foreign body implant has a semi-firm consistency.

In accordance with another embodiment, the foreign body implant is radio opaque.

In accordance with another embodiment, the foreign body implant is capable of being visually located when a light is shined through the breast.

In accordance with another embodiment, the foreign body implant is luminescent.

In accordance with another embodiment, the foreign body implant is fabricated from one of (1) soft plastic, (2) soft rubber, and (3) silicone.

In accordance with another embodiment, the foreign body implant includes a cystic shell filled with at least one of (1) a saline solution, (2) mineral oil, (3) olive oil, and (4) a silicone gel.

Other possible embodiments, in addition to the possible embodiments enumerated above, will become apparent from the following detailed description, taken in conjunction with the accompanying drawings, which illustrate, by way of example, the principles of the implant and method of use.

DETAILED DESCRIPTION OF THE INVENTION

Figure 1:
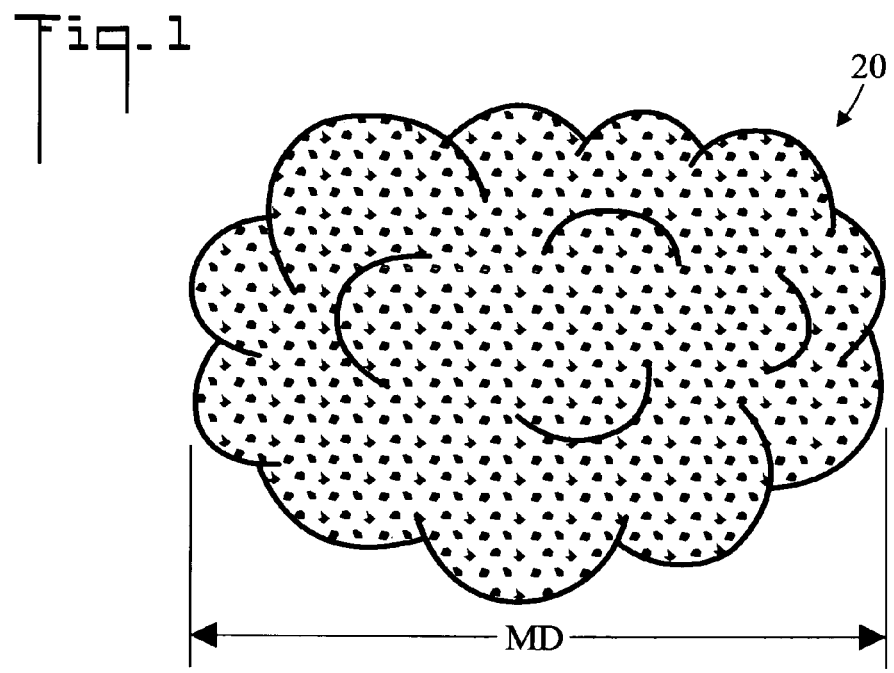
FIG. 1 is an enlarged view of a device for improving the early detection of breast cancer.
Figure 2:
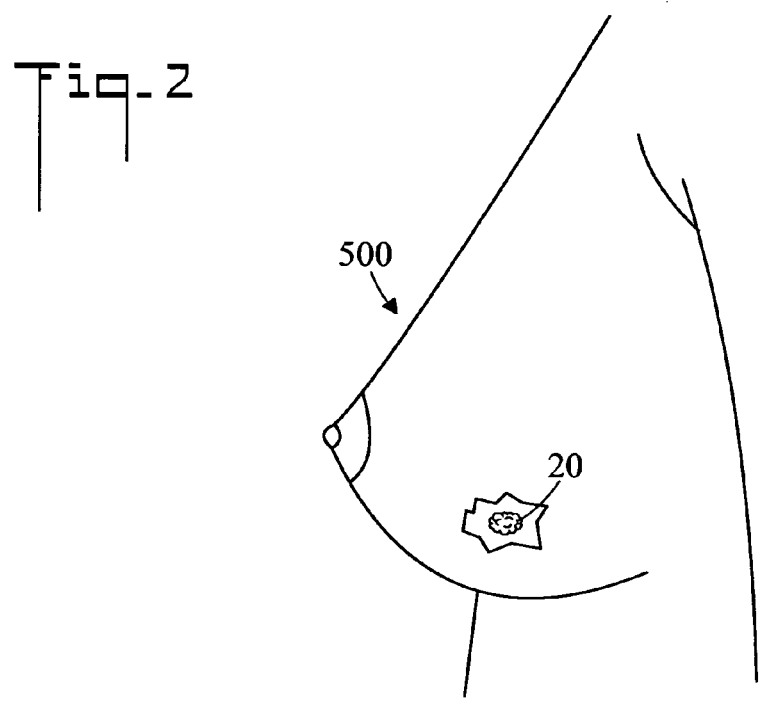
FIG. 2. is a side elevation cutaway view showing the placement of the device in the breast of a human being; and, FIG. 3 is a front elevation cutaway view showing an alternate placement of the device in the abdominal wall of the human being.

Referring initially to FIG. 1, there is illustrated an enlarged view of a device for improving the early detection of breast cancer. FIG. 2. is a reduced side elevation cutaway view showing the placement of the device in the breast 500 of a human being. The device comprises a foreign body implant 20 which is shaped and dimensioned to imitate (i.e. feel like) a breast tumor, and which provides a tactile standard with which to compare a possible breast cancer tumor. Foreign body implant 20 has an asymmetrical shape, and is implantable in the breast 500 of human being. In an embodiment, foreign body implant 20 has a maximum dimension MD of about seven millimeters. For example foreign body implant 20 could be 7 mm wide by 5 mm high by 6 mm deep, 6 mm wide by 4 mm high by 5 mm deep, 5 mm wide by 3 mm high by 4 mm deep, etc. The reason for using a small size foreign body implant is to simulate Stage 1 breast cancer which has a 98% five year survival rate after successful treatment. The reason for the asymmetrical shape is to imitate tumors which have an irregular and non-round shape. In an embodiment, foreign body implant 20 has an irregular surface. For example the surface is uneven such as pebbly and/or granular. Alternatively the surface may contains depressions such as those of a golf ball.

Figure 3:
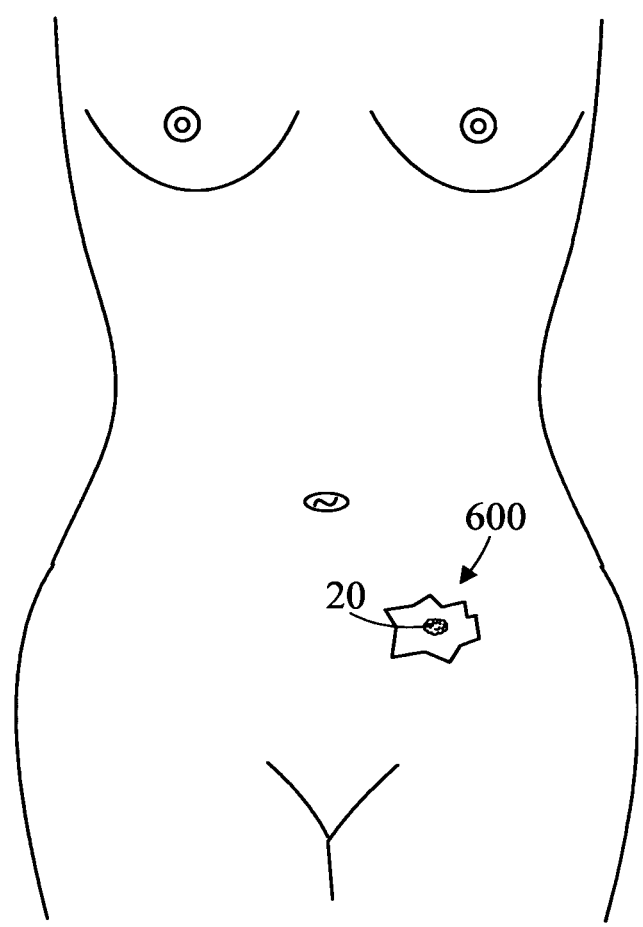

In an embodiment, foreign body implant 20 has a semi-firm consistency (e.g. like a slice of raw carrot). In another embodiment, foreign body implant 20 can be fabricated from one of (1) soft plastic, (2) soft rubber, and (3) silicone. Also, foreign body implant 20 can include a cystic shell which is filled with at least one of (1) a saline solution, (2) mineral oil, (3) olive oil, and (4) a silicone gel. In another embodiment, foreign body implant 20 is radio-opaque so that it can be seen in an X-ray. In another embodiment, foreign body implant 20 is capable of being visually located by light diffusion when a light (such as a flashlight) is shined through breast 500 in a dark environment. In another embodiment foreign body implant 20 can be luminescent FIG. 2 shows foreign body implant 20 implanted in a breast 500, and FIG. 3 shows foreign body implant 20 implanted in the anterior abdominal wall 600 of a person. The cutaway view shown by the zig-zag line indicates that foreign body implant 20 is implanted beneath the skin of the person. As such, foreign body implant 20 improves the effectiveness of breast cancerous tumor detection. Foreign body implant 20 increases the efficacy of both BSE and breast clinical examination for the detection of human breast cancer. The postoperative foreign body implant 20 will be freely mobile and detached from the surrounding soft tissue. A few weeks later the surrounding fibrosis will stabilize foreign body implant 20. Foreign body implant 20 is preferably implanted in any breast 500 quadrant except the outer upper quadrant since the upper outer quadrant (UOQ) of breast 500 is the most frequent site for incidence of breast cancer Foreign body implant 20 is used in high risk patients for breast cancer, however all women above 50 years of age can benefit from foreign body implant 20. Foreign body implant 20 is implanted in the breast 500 or the anterior abdominal wall 600. After the implant heals, and during each periodic breast self-examination (typically monthly), the woman feels foreign body implant 20 to reinforce her tactile memory of breast cancer/tumors. If during the BSE the woman finds a new lump or distortion, that lump or distortion can be compared with foreign body implant 20 to better identify a possible incidence of breast cancer.

Foreign body implant 20 is implanted about 1.5 cm deep in soft tissue of the breast, but it can be variable in depth according to the breast size. In a woman having large breasts, a 7 mm foreign body implant 20 can be implanted more deeply (e.g. 2 cm), Conversely in a women having small breasts, a 5 mm foreign body implant 20 can be implanted more superficially (e.g. 1 cm). Foreign body implant 20 is implanted in either adipose or glandular tissue. Also, foreign body implant 20 can be implanted in the soft tissue of the anterior abdominal wall. Foreign body implant 20 can be implanted under local anesthesia. The duration of the implant is life-long.

In terms of use, a method for improving the early detection of breast cancer in a human being having a breast 500 and an abdominal wall 600 includes:

(a) providing a foreign body implant 20 which is shaped and dimensioned to imitate a breast tumor;

(b) surgically implanting foreign body implant 20 in at least one of (1) breast 500 of the human being; and, (2) the abdominal wall 600 of the human being; and, (c) after step (b), on a periodic basis the human being performing breast self examination, the breast self examination including feeling foreign body implant 20 to reinforce a tactile memory of breast tumors.

The method further including:

in step (a), foreign body implant 20 having an asymmetrical shape, being radio opaque, having a maximum dimension of about seven millimeters, having an irregular surface, and having a semi-firm consistency.

The method further including:

in step (b), implanting foreign body implant 20 between about one centimeter and about two centimeters deep in the breast of the human being.

The breast 500 of the human being including both adipose and glandular tissue, the method further including:

in step (b), implanting foreign body implant 20 in at least one of the adipose and glandular tissue.

The breast having an outer upper quadrant, the method further including:

in step (b), not implanting foreign body implant 20 in the outer upper quadrant.

The method further including:

during step (c), the woman comparing the feel of a possible breast tumor with the feel of foreign body implant 20.

The method further including:

performing steps (a) through (c) on at least one of (1) women over 50 years of age, and (2) women with a high risk for breast cancer.

The possible embodiments of the implant and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the foreign body implant and method of use should be construed as limiting the invention to a particular embodiment or combination of embodiments. The scope of the invention is best defined by the appended claims.

We claim:

1. A device for improving the early detection of a breast cancer tumor in the breast of a human being, comprising:
   a foreign body implant which simulates the shape and consistency of the breast cancer tumor;

said foreign body implant implantable in the breast of the human being;

said foreign body implant providing a tactile standard with which to compare the breast cancer tumor; and, said foreign body implant having a semi-firm consistency like that of a slice of raw carrot.

2. A device for improving the early detection of a breast cancer tumor in the breast of a human being, comprising:

a foreign body implant which simulates the shape and consistency of the breast cancer tumor;

said foreign body implant implantable in the breast of the human being;

said foreign body implant providing a tactile standard with which to compare the breast cancer tumor; and, said foreign body implant being luminescent.

3. A device for improving the early detection of a breast cancer tumor in the breast of a human being, comprising:

a foreign body implant which simulates the shape and consistency of the breast cancer tumor;

said foreign body implant implantable in the breast of the human being;

said foreign body implant providing a tactile standard with which to compare the breast cancer tumor;

said foreign body implant having a maximum dimension of about seven millimeters;

said foreign body implant having an irregular surface; and, said foreign body implant having a semi-firm like that of a slice of raw carrot.

* * * * *